US00PP12098P2

(12) United States Plant Patent
Snyder

(10) Patent No.: US PP12,098 P2
(45) Date of Patent: Sep. 18, 2001

(54) FUJI APPLE TREE NAMED 'SNYDER'

(75) Inventor: Richard L. Snyder, Wenatchee, WA (US)

(73) Assignee: Snyder, Wenatchee, WA (US)

( * ) Notice: Subject to any disclaimer, the term of this patent is extended or adjusted under 35 U.S.C. 154(b) by 0 days.

(21) Appl. No.: 09/422,865

(22) Filed: Oct. 21, 1999

(51) Int. Cl.[7] ..... A01H 5/00

(52) U.S. Cl. ..... Plt./168

(58) Field of Search ..... Plt./768

*Primary Examiner*—Bruce R. Campell
*Assistant Examiner*—Annette H. Para
(74) *Attorney, Agent, or Firm*—Klarquist Sparkman Campbell Leigh & Whinston LLP

(57) ABSTRACT

A new and distinct variety of Fuji apple tree named 'Snyder' having an intense and uniform red stripe pattern over the entire fruit surface and semi-spur growth habit.

3 Drawing Sheets

BACKGROUND OF THE INVENTION

The present invention relates to a new and distinct strain of Fuji apple tree which is referred to by the varietal name 'Snyder'.

Five adjacent trees of this variety were discovered by me in the summer of 1994 in a block of 'BC 2' Fuji apple trees (unpatented). These trees had been grafted on 'Malling 26' ('M26') rootstock (unpatented) and were growing in a cultivated area of a nursey in Quincy, Wash. I noticed that these trees of my new variety were distinctly different in appearance (smaller in size) from the adjacent 'BC2' Fuji trees. The trees of my new variety were tagged and dug in October, 1994, and they were placed in storage until Spring, 1995, when they were planted with other selected strains of Fuji apple trees in a test orchard at Orondo, Wash. First fruiting of these trees of my new variety occurred in 1997, which showed that fruit from the trees of my new variety showed heavy striping, full coloration, and distinct differences from the fruits of standard Fuji (unpatented), 'BC2' Fuji (unpatented), 'Akisaka Spur' Fuji (unpatented), 'Nagafu 6' Fuji (unpatented, 'Nagafu 12' Fuji (unpatented), 'Myra' Fuji (U.S. Plant Pat. No. 9,645), and 'TAC 114' Fuji (U.S. Plant Pat. No. 8,8032). Based upon my observations of these initial five trees and of asexually propagated progeny, I have concluded that the 'Snyder' variety is a new and distinct Fuji cultivar. I have also concluded that my new variety must have developed as a limb mutation of 'BC 2', and that a single mutated budstick produced the five trees of my variety which were originally found at Quincy, Wash.

My new variety has been observed to be of a semi-spur nature. The blooms, limb characteristics, and the size and color of the leaves of the new 'Snyder' Fuji strain are identical to 'BC 2' Fuji insofar as I have been able to observe.

DETAILED DESCRIPTION

Figure 1:
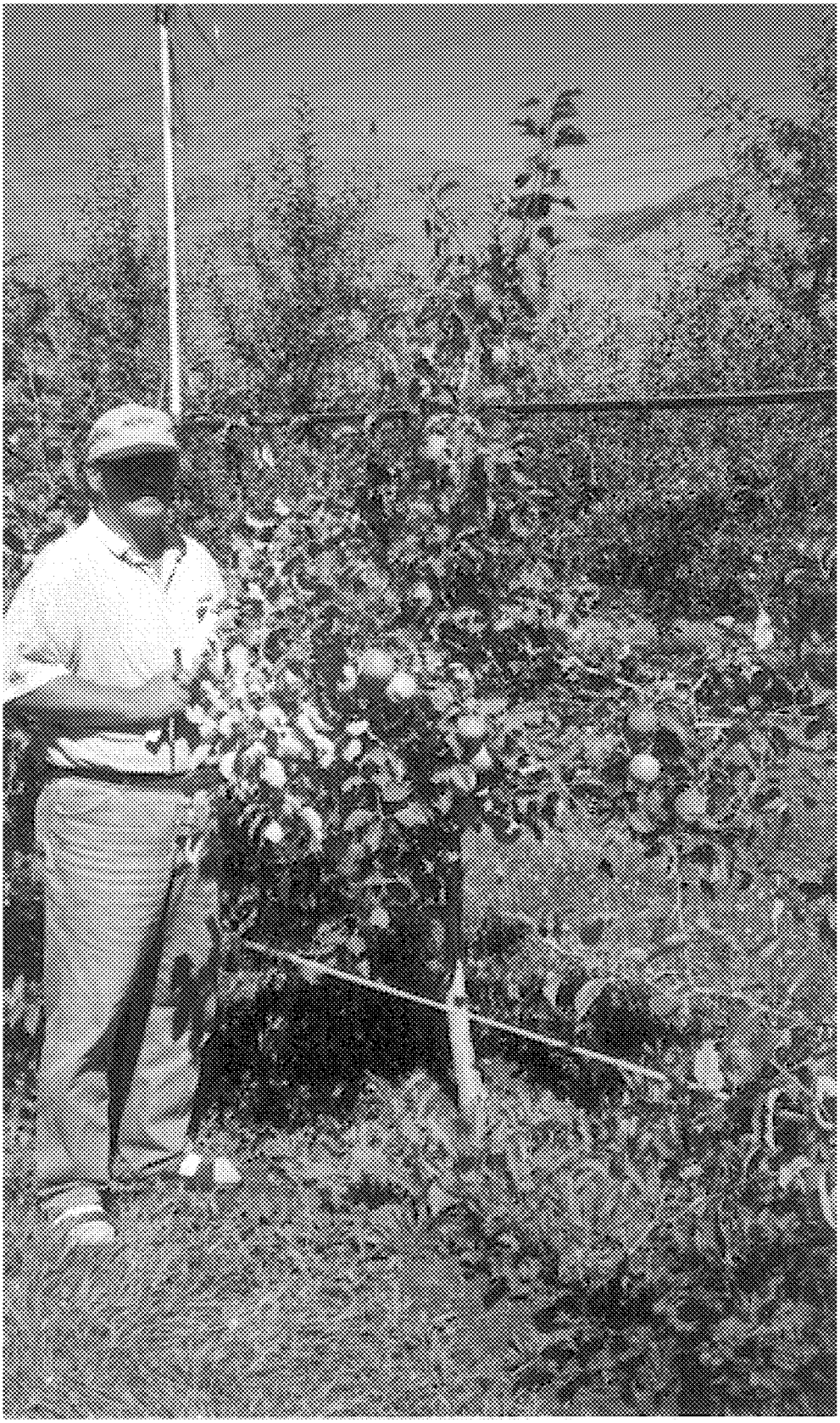
FIG. 1 Shows a 'Snyder' Fuji tree.
Figure 2:
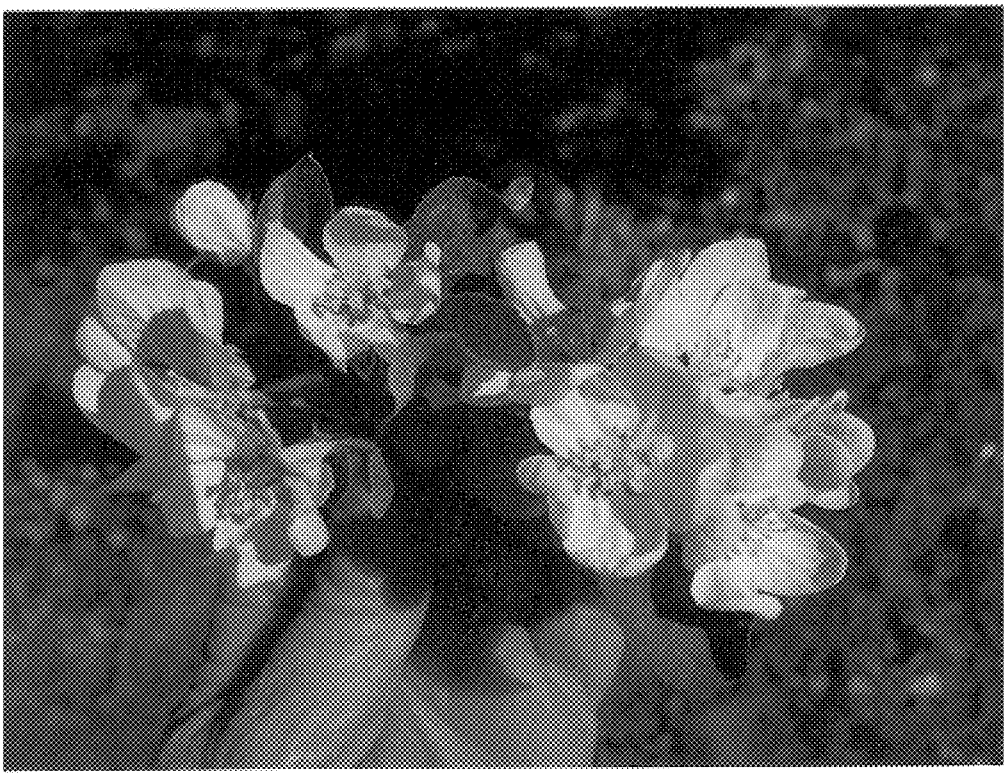
FIG. 2 Shows blooms of my new variety.
Figure 3:
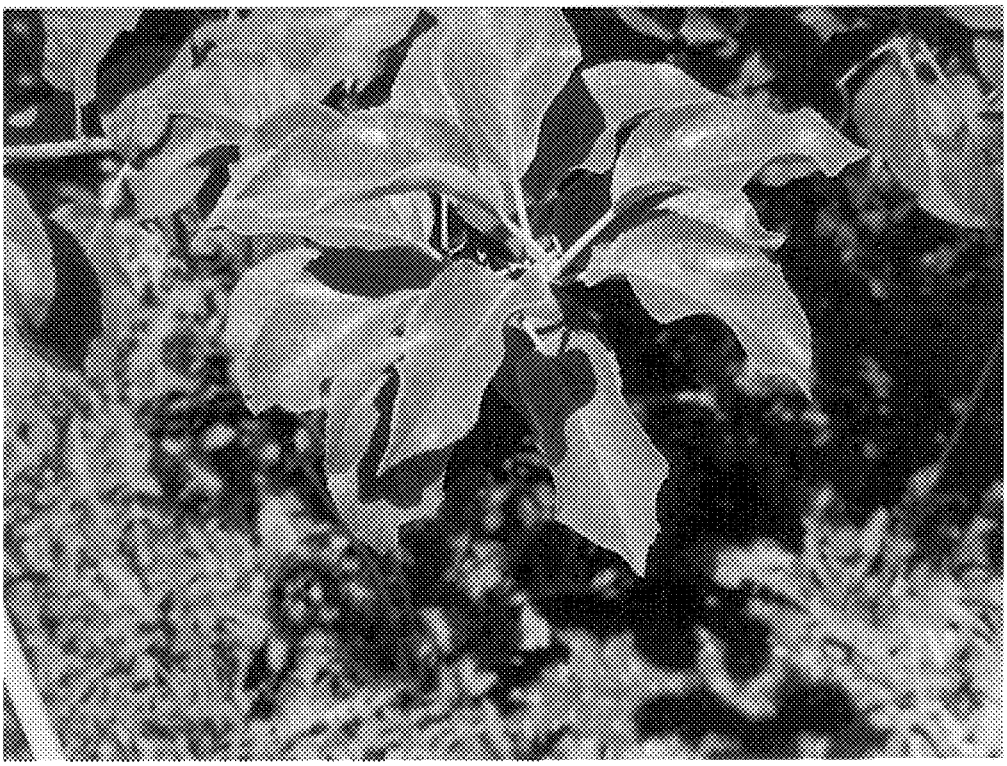
FIG. 3 Shows leaves of my new variety.
Figure 4:
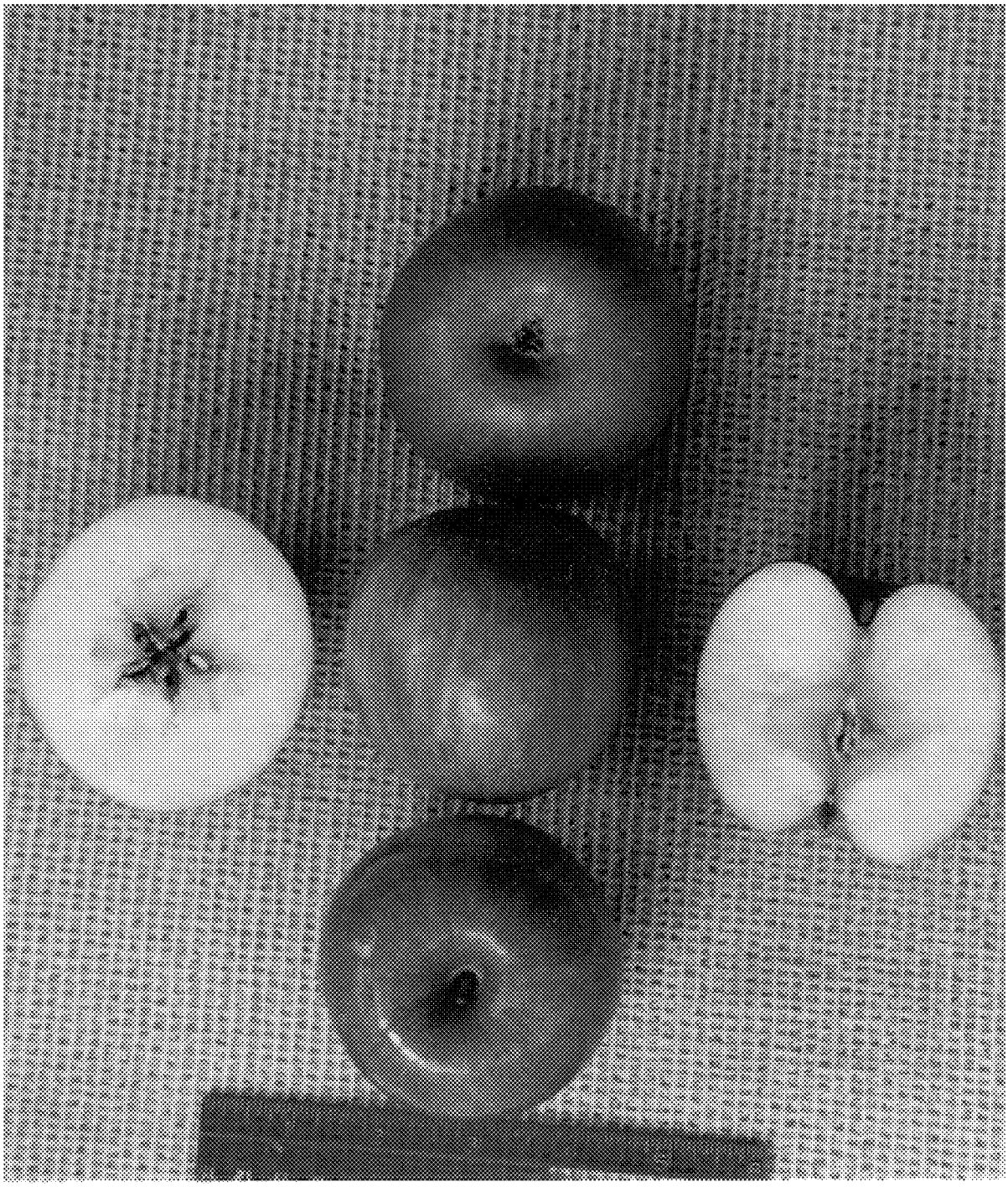
FIG. 4 Shows fruit of my new variety; including longitudinal and transverse sections of the fruit and entire fruit.

The following is a detailed description of my invention based on observations at Quincy, Wash. and Orondo, Wash. These observations were of the original trees and also of progeny which were asexually propagated by grafting on 'M26' rootstock at Orondo, Wash. These observations have confirmed that the characteristics of my new variety are fixed.

The following is a description of the characteristics of my new 'Snyder' Fuji apple tree (*Malus pumila* Mill) about 5 years of age. Color references are to the Munsell Book of Color (MBC). It should be understood that colors can vary due a number of factors, such as environmental growing conditions for the trees and lighting conditions under which color observations are made.

Tree: Medium size, somewhat spreading, slightly less vigor than 'BC 2' Fuji. Average size of trees at Orondo, Wash. at five years from planting:

*Height.*—8 to 10 feet.

*Diameter.*—About 7 to 9 feet.

*Caliper.*—About 3 to 5 inches at 12 inches above ground.

*Trunk.*—Stocky, smooth.

*Trunk bark texture.*—Smooth, with prominent lenticels.

*Trunk bark color.*—Brownish grey, MBC #2.5Y 6/2 .

*Branches.*—Spreading, wide angles, 45–90 degrees at emergence.

*Branch color.*—one-year dormant shoot, MBC #5/YR 3/4; two-year branch, MBC #10YR 5/2.

*Branch pubescence.*—Heavy on new wood, becoming glabrous on older wood; color of new wood is MBC #2.5Y 8.5/2.

*Branch lenticels.*—Observed to be medium in density (about 8–10 per sq. cm), elongated (1×2 mm) and tan in color, MBC #2.5Y 8.5/2.

*Internodes.*—Average length on one-year-old shoots—27.7 mm, compared to avarage of 41.0 mm on 'BC 2' Fuji (average of 27 measurements).

*Bearing.*—Annual to occasionally biennial; heavy, similar to the 'BC2' Fuji tree.

*Hardiness.*—Similar to standard Fuji.

*Disease and insect resistance.*—Similar to standard Fuji; no unusual resistance or susceptibility observed as of this time.

Leaves (primary): Broad, dark green, medium glossy on upper surface, finely pubescent on lower surface.

*Length.*—(Average of 10 leaves in May, 1999 at Orondo, Wash.). Range about 60 to 100 mm; average 76 mm.

*Width.*—Range about 40 to 60 mm; average 51 mm.

*Petiole.*—Medium length range about 20 to 30 mm; 1.7 to 1.9 mm thick; finely pubescent.

*Margin.*—Finely serrate.

*Tip.*—Sharply pointed.

*Stipules.*—In pairs, thin, pointed, 10 mm in length.

*Color.*—MBC #5GY 4/8 on upper surface, MBC #5GY 6/4 on lower surface.

*Pubescence.*—Fine, along veins on upper surface; fine and totally covering lower surface.

Flowers: Identical to those of 'BC 2' Fuji; first bloom midseason (Apr. 29, 1999, in Orondo, Wash.); full bloom approximately May 1, 1999; bloom duration approximately 18 days. Varies with growing conditions.

*Size.*—Medium to large, approximately 40–50 mm in diameter; petals observed to be 26×20 mm.

*Color.*—Purplish pink (unopened); white (opened); bud some red, MBC #2.5R 7/6.

*Petals.*—Numbering about five, touching to overlapping at margin, about 22 mm long and 15 mm wide; petals are white on both upper and lower surfaces, with a slight tinge of pink, MBC #2.5R 7/6, on the lower petal surface.

*Stamen.*—About 15 in number, single row, with approximately 15 anthers; bright yellow, MBC #2.5Y 8.5/12; about 10 mm in length.

*Pollen color.*—Bright yellow, MBC #2.5Y 8.5/12.

*Pistil.*—One in number, stigma medium length, flat at top, rounded at base with 5 styles, fused at base, colored MBC #2.5GY 8/8, and about 12 mm in length.

*Sepals.*—Numbering about 5, medium size, pubescent, 10 mm long×3 mm wide at base, recurved downward, wedge shaped, and color MBC #2.5GY 7/7.

*Pollination requirements.*—Believed compatible with all cultivars except Fuji, which bloom in the same time period.

*Fragrance.*—Light, no apparent difference from other apple blossoms.

Fruit: Maturity when described was mid-harvest period (mid-October 1998); firmness 17 to 20 pounds; soluble solids 14 to 16% ; starch index (1–6 scale) 3 to 3.5, and acid content 0.4% malic acid. Samples were stored until Jun. 1, 1999, in common storage (0 to 2 degrees C.) and sampled periodically for condition and eating quality.

*Size.*—Medium to large, box size 72 (83.6 mm) to 100 (74.4 mm).

*Form.*—Round to oblong, occasionally oblate, usually symmetric; length/diameter ratio 1:1, with ribbing absent, lacking lobes at the calyx end.

*Cavity.*—Broad, medium depth (15 mm).

*Basin.*—Medium depth (10 mm); medium width (30 to 35 mm); lightly pubescent at the base.

*Stem.*—Medium length (26 mm,), medium thickness (2.2 mm).

*Locules* (*carpels*).—Medium to small, 5 in number, tight, closed.

*Skin.*—Thin, tender, glossy, very slow to become oily in storage, not prone to russet, slight tendency to cracking around cavity as fruit becomes over-mature.

*Lenticles.*—MBC #7.5Y 8.5/6; small, round, inconspicuous.

*General color effect.*—Prominently striped, more prominent than any red Fuji strain yet observed, including 'BC 2', 'Nagafu 2', 'Nagafu 6', and 'Nagafu 12', and 'Myra'.

*Ground color.*—MBC #5Y 8/10 MBC #at optimum maturity, from 10 Y 8/10 at early picking maturity.

*Overcolor.*—Prominent stripe, MBC #5R 4/10 over a lighter blush, MBC #7.5R 6/10.

*Russet.*—Generally absent, but similar to standard Fuji, which can show occasional russet caused by environment or caustic sprays.

*Flesh.*—Color of flesh cream (MBC #5Y 8.5/4); very juicy, sweet, 12 to 15 Brix, non-astringent, mild flavor; low acidity, approximately 0.4% malic acid; moderate aroma; firmness 18 to 20 pounds at harvest.

*Core.*—Bundle area round, average width of core 27 mm, average length 23 mm, 10 bundles; core lines weakly defined; locules are closed; cell walls thin (not measured), giving strong sensation of crispness and juiciness, calyx tube short, closed.

*Seed.*—Seeds number mostly 2 per cell; shape obovate; color MBC #7.5YR 3/6 (reddish brown); typical size 8 mm (length)×5 mm (width), tightly adhering to the carpel wall.

*Storage.*—Keeping quality is similar to that of standard Fuji, e.g., excellent. Fruit remains crisp at room temperature for 2 weeks or more. Quality can be maintained up to 9 months in common storage (0 degrees C.), and up to 12 months in controlled atmosphere (CA) storage.

*Usage.*—Primarily fresh eating (dessert); can be used for culinary purposes, especially in low-sugar recipes.

*Resistance to pests and diseases.*—For both the tree and fruit, identical to standard Fuji apple trees and other commonly used Fuji varieties known to the inventor.

What is claimed:

1. A new and distinct variety of the Fuji apple tree named 'Snyder' as illustrated and described herein, particularly characterized by an intense and uniform red stripe pattern over the entire fruit surface and a semi-spur growth habit.

* * * * *

UNITED STATES PATENT AND TRADEMARK OFFICE

CERTIFICATE OF CORRECTION

PATENT NO. : PP 12,098 P2
DATED : September 18, 2001
INVENTOR(S) : Snyder, Richard L.

It is certified that error appears in the above-identified patent and that said Letters Patent is hereby corrected as shown below:

Column 1,
Line 24, the number "8,8032" should be -- 8032 --

Column 2,
Line 41, the word "avarage" should be -- average --

Column 3,
Line 44, the number "7/7" should be -- 7/4 --

Column 4,
Lines 20-21, the phrase "8/10 MBC #at optimum maturity, from 10 Y" should be -- 8/10 at optimum maturity, from MBC #10Y --

Signed and Sealed this

Fourth Day of June, 2002

*Attest:*

*Attesting Officer*

JAMES E. ROGAN
*Director of the United States Patent and Trademark Office*